(12) United States Patent
Webb

(10) Patent No.: US 11,562,637 B1
(45) Date of Patent: Jan. 24, 2023

(54) EVENT BASED MONITORING OF A PERSON

(71) Applicant: Vivint, Inc., Provo, UT (US)

(72) Inventor: Adam K. Webb, Provo, UT (US)

(73) Assignee: VIVINT, INC., Provo, UT (US)

( * ) Notice: Subject to any disclaimer, the term of this patent is extended or adjusted under 35 U.S.C. 154(b) by 0 days.

(21) Appl. No.: 16/828,777

(22) Filed: Mar. 24, 2020

Related U.S. Application Data

(63) Continuation of application No. 15/094,691, filed on Apr. 8, 2016, now Pat. No. 10,600,305.

(51) Int. Cl.
  *G08B 21/04* (2006.01)
  *H04N 7/18* (2006.01)
  *G16H 40/63* (2018.01)
  *G08B 13/196* (2006.01)

(52) U.S. Cl.
  CPC ....... *G08B 21/0453* (2013.01); *G08B 13/196* (2013.01); *G08B 13/19684* (2013.01); *G16H 40/63* (2018.01); *H04N 7/18* (2013.01); *H04N 7/188* (2013.01)

(58) Field of Classification Search
  CPC .......... H04N 7/188; H04N 7/18; G16H 40/63; G08B 13/19684; G08B 21/0453; G08B 13/196
  See application file for complete search history.

(56) References Cited

U.S. PATENT DOCUMENTS

| | | | |
|---|---|---|---|
| 5,684,460 A | 11/1997 | Scanlon | |
| 9,131,328 B2 * | 9/2015 | Kobylarz | H04W 4/00 |
| 2002/0103512 A1 | 8/2002 | Echauz et al. | |
| 2002/0167403 A1 | 11/2002 | Colmenarez et al. | |
| 2006/0178567 A1 * | 8/2006 | Goh | G01S 5/0009 600/300 |
| 2006/0190419 A1 | 8/2006 | Bunn et al. | |
| 2008/0266118 A1 * | 10/2008 | Pierson | A61B 5/6826 340/573.6 |
| 2010/0152600 A1 * | 6/2010 | Droitcour | A61B 5/1114 600/534 |
| 2010/0191074 A1 | 7/2010 | Chou | |
| 2010/0298683 A1 | 11/2010 | Cabrera et al. | |
| 2012/0075464 A1 | 3/2012 | Derenne et al. | |
| 2013/0002434 A1 | 1/2013 | Cuddihy et al. | |
| 2013/0182107 A1 | 7/2013 | Anderson | |
| 2013/0229283 A1 | 9/2013 | Receveur et al. | |

(Continued)

*Primary Examiner* — Neil R Mikeska
(74) *Attorney, Agent, or Firm* — Kunzler Bean & Adamson

(57) ABSTRACT

In some instances, a person may need monitoring. The monitoring may be based on age, or on other factors such as abilities and functionality. The monitoring may enable a supervising person to remotely receive updates regarding the subject person. The supervising person may enter in various biometric parameters to monitor. The supervising person may alternatively and/or additionally set other factors to monitor such as time of day, location, activity level, and the like. The monitoring may provide peace of mind to a supervising person to ensure the subject person is safe. In some embodiments, the supervising person may set various alarm thresholds. The alarm thresholds may trigger an alert to the supervising person. In alternative embodiments, if the subject person is a grown person without a supervising person in the same vicinity, a security and/or automation system may act as the supervising adult.

20 Claims, 7 Drawing Sheets

(56) References Cited

U.S. PATENT DOCUMENTS

| | | |
|---|---|---|
| 2014/0247153 A1 | 9/2014 | Proud |
| 2014/0257047 A1 | 9/2014 | Sillay et al. |
| 2014/0306833 A1 | 10/2014 | Ricci |
| 2015/0094914 A1* | 4/2015 | Abreu ............... B60H 1/00742 701/41 |
| 2015/0160636 A1* | 6/2015 | McCarthy, III ........ G05B 15/02 348/552 |
| 2015/0223705 A1* | 8/2015 | Sadhu ................. G08B 21/0446 600/301 |
| 2015/0223731 A1 | 8/2015 | Sahin |
| 2015/0231387 A1* | 8/2015 | Harding ............... A61N 1/0456 600/393 |
| 2015/0379238 A1 | 12/2015 | Connor |
| 2016/0054977 A1 | 2/2016 | Gritton et al. |
| 2016/0072891 A1* | 3/2016 | Joshi ................. G06Q 30/0631 370/254 |
| 2016/0142407 A1* | 5/2016 | Chun ..................... H04L 63/12 726/5 |
| 2016/0228640 A1* | 8/2016 | Pindado ............. A61N 1/36139 |
| 2017/0108236 A1* | 4/2017 | Guan .................... H05B 47/105 |
| 2017/0122774 A1* | 5/2017 | Quady ................... G01D 4/002 |
| 2017/0156608 A1* | 6/2017 | Mahar .................. A61B 5/0205 |
| 2017/0344717 A1 | 11/2017 | Houlihan |
| 2018/0020194 A1 | 1/2018 | Kim |
| 2018/0035901 A1* | 2/2018 | Cronin ................ A61B 5/0022 |

\* cited by examiner

EVENT BASED MONITORING OF A PERSON

RELATED APPLICATIONS

This application is a continuation of U.S. patent application Ser. No. 15/094,691, filed Apr. 8, 2016, and entitled EVENT BASED MONITORING OF A PERSON, the disclosure of which is incorporated herein by this reference.

BACKGROUND

The present disclosure, for example, relates to security and/or automation systems, and more particularly to monitoring subject personnel based on various biometric parameters.

Security and automation systems are widely deployed to provide various types of communication and functional features such as monitoring, communication, notification, and/or others. These systems may be capable of supporting communication with a user through a communication connection or a system management action.

Often times, people want to know their loved ones are safe. The loved one may be vulnerable and have health concerns. For example, a parent may want to monitor a child, an adult may wish to monitor a special needs child, an adult with a disability and/or disease may require remote monitoring.

SUMMARY

In some instances, a person may be monitored. The monitoring may be based on age, or on other factors such as abilities and functionality. The monitoring may enable a supervising person to remotely receive updates regarding the subject person. The supervising person may enter in various biometric parameters to monitor. The supervising person may alternatively and/or additionally set other factors to monitor such as time of day, location, activity level, and the like. The monitoring may provide peace of mind to a supervising person to ensure the subject person is safe. In some embodiments, the supervising person may set various alarm thresholds. The alarm thresholds may trigger an alert to the supervising person. In alternative embodiments, if the subject person is a grown person without a supervising person in the same vicinity, a security and/or automation system may act as the supervising adult.

In one embodiment, a method for security and/or automation systems is described. The method may include monitoring a set of biometric parameters associated with a subject person and obtaining visual surveillance of the subject person while monitoring the biometric parameters. The method may additionally include detecting an active alarm status based at least in part on the monitoring and providing the visual surveillance of the subject person when an alarm threshold is satisfied during the active alarm status.

In further embodiments, the method may include receiving input to monitor the set of biometric parameters and setting alarm thresholds for the biometric parameters. In another embodiment the method may include determining when the alarm threshold is satisfied and activating an audible alarm when the alarm threshold is satisfied. In another instance the method may include customizing the biometric parameters and alarm thresholds to the subject person.

In some embodiments, the method may include determining when the alarm threshold is satisfied and activating an audio-visual alarm when the alarm threshold is satisfied. The method may also include recording biometric parameter readings and visual surveillance associated with the biometric parameter readings and storing the biometric parameter readings and visual surveillance in a database based at least in part on the recording.

In some embodiments monitoring the biometric parameters may also include detecting at least one of a respiration rate, or a body temperature, or movement data, or auditory data, or a combination thereof. The method may also include deactivating the alarm based at least in part on input from a user. The method may alternatively include requesting emergency personnel assistance based at least in part on user input.

In some embodiments, the method may include automatically transferring biometric parameters readings to the emergency personnel based at least in part on the requesting. The method may include automatically contacting emergency personnel when biometric parameter thresholds are satisfied.

In another embodiment, an apparatus for security and/or automation systems is described. The apparatus may include a processor, memory in electronic communication with the processor, and instructions stored in the memory. The instructions may be executable by the processor to monitor a set of biometric parameters associated with a subject person, obtain visual surveillance of the subject person while monitoring the biometric parameters, detect an active alarm status based at least in part on the monitoring, and provide the visual surveillance of the subject person when an alarm threshold is satisfied during the active alarm status.

In a further embodiment, a non-transitory computer-readable medium storing computer-executable code is described. The code may be executable by a processor to monitor a set of biometric parameters associated with a subject person, obtain visual surveillance of the subject person while monitoring the biometric parameters, detect an active alarm status based at least in part on the monitoring, and provide the visual surveillance of the subject person when an alarm threshold is satisfied during the active alarm status.

The foregoing has outlined rather broadly the features and technical advantages of examples according to this disclosure so that the following detailed description may be better understood. Additional features and advantages will be described below. The conception and specific examples disclosed may be readily utilized as a basis for modifying or designing other structures for carrying out the same purposes of the present disclosure. Such equivalent constructions do not depart from the scope of the appended claims. Characteristics of the concepts disclosed herein—including their organization and method of operation—together with associated advantages will be better understood from the following description when considered in connection with the accompanying figures. Each of the figures is provided for the purpose of illustration and description only, and not as a definition of the limits of the claims.

BRIEF DESCRIPTION OF THE DRAWINGS

A further understanding of the nature and advantages of the present disclosure may be realized by reference to the following drawings. In the appended figures, similar components or features may have the same reference label. Further, various components of the same type may be distinguished by following a first reference label with a dash and a second label that may distinguish among the similar components. However, features discussed for various components—including those having a dash and a second reference label—apply to other similar components. If only the first reference label is used in the specification, the description is applicable to any one of the similar components having the same first reference label irrespective of the second reference label.

DETAILED DESCRIPTION

Some people may require supervision. The various levels and type of supervision may vary, but a supervising person may want to have select monitoring available to know the subject person (the person being monitored) is safe and healthy. Each individual subject person may require different monitoring parameters. For example, a parent may wish to monitor an infant when the infant naps or at nighttime. A parent of an older child may only wish to monitor the child for various noises throughout the bedroom at night. If a subject person has a disability or illness, the supervising person may wish to monitor various biometric parameters associated with the disability or illness. For example, if a person has epilepsy, the supervising person may wish to be notified if the subject person has an attack. The supervising person may wish to receive visual recordings of the attack to ensure the person is safe. Similarly, a parent may wish to review a child's nighttime history for any peculiarities in the child's recorded biometric parameters. If a peculiarity exists, the parent may wish to view visual recording of the event to determine if corrective action needs to be taken or for simple piece of mind. These types of features may additionally be helpful for an adult living independently but subject to various ailments.

The following description provides examples and is not limiting of the scope, applicability, and/or examples set forth in the claims. Changes may be made in the function and/or arrangement of elements discussed without departing from the scope of the disclosure. Various examples may omit, substitute, and/or add various procedures and/or components as appropriate. For instance, the methods described may be performed in an order different from that described, and/or various steps may be added, omitted, and/or combined. Also, features described with respect to some examples may be combined in other examples.

Figure 1:
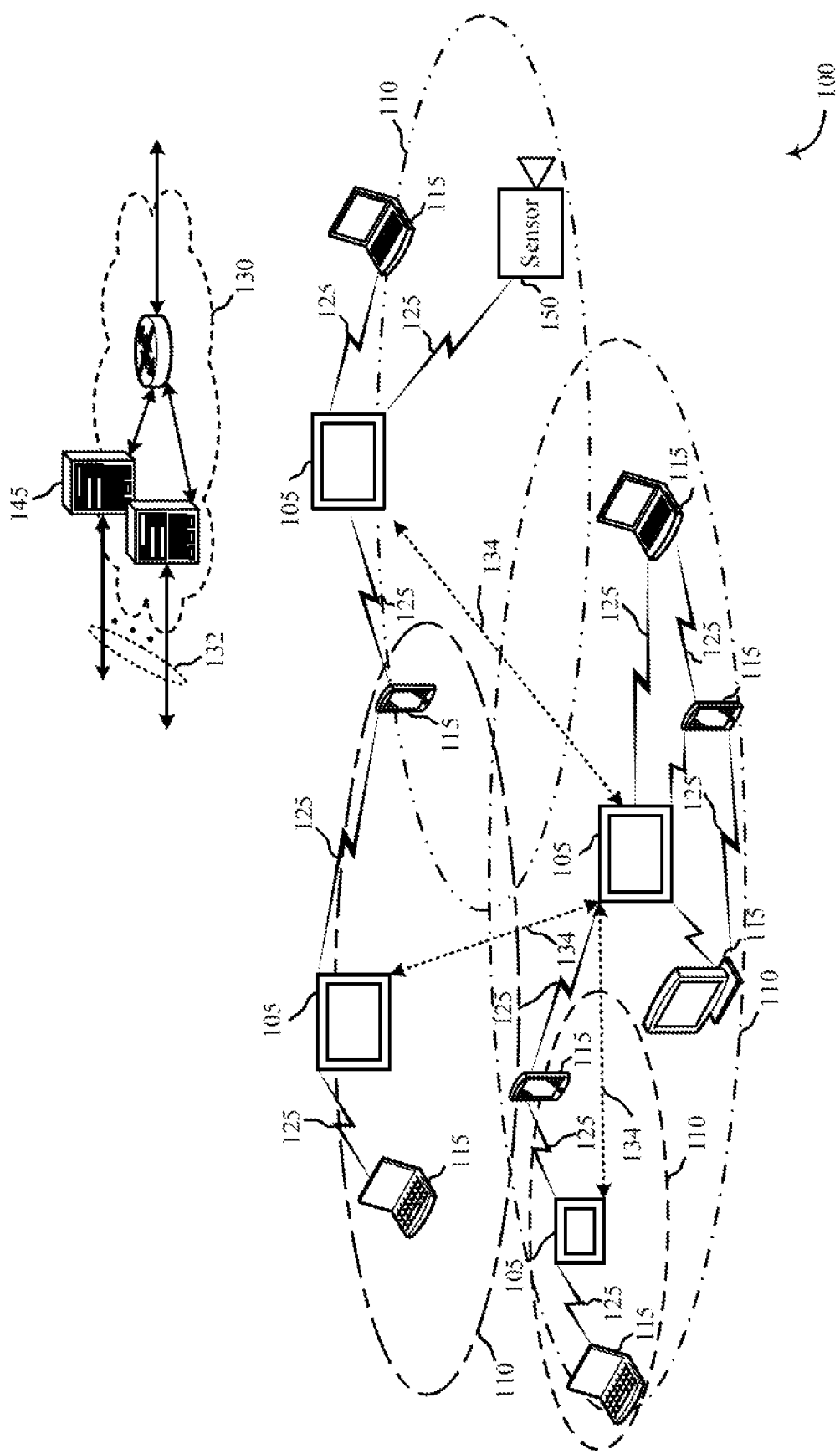
FIG. 1 shows a block diagram relating to a security and/or an automation system, in accordance with various aspects of this disclosure.

FIG. 1 illustrates an example of a communications system 100 in accordance with various aspects of the disclosure. The communications system 100 may include control panels 105, devices 115, a network 130, and/or sensors 150. The network 130 may provide user authentication, encryption, access authorization, tracking, Internet Protocol (IP) connectivity, and other access, calculation, modification, and/or functions. The control panels 105 may interface with the network 130 through a first set of wired and/or wireless communication links 132 to communicate with one or more remote servers 145. The control panels 105 may perform communication configuration, adjustment, and/or scheduling for communication with the devices 115, or may operate under the control of a controller. In various examples, the control panels 105 may communicate—either directly or indirectly (e.g., through network 130)—with each other over a second set of wired and/or wireless communication links 134. Control panels 105 may communicate with a back end server (such as the remote servers 145)—directly and/or indirectly—using the first set of one or more communication links 132.

The control panels 105 may wirelessly communicate with the devices 115 via one or more antennas. Each of the control panels 105 may provide communication coverage for a respective geographic coverage area 110. In some examples, control panels 105 may be referred to as a control device, a base transceiver station, a radio base station, an access point, a radio transceiver, or some other suitable terminology. The geographic coverage area 110 for a control panel 105 may be divided into sectors making up only a portion of the coverage area. The communications system 100 may include control panels 105 of different types. There may be overlapping geographic coverage areas 110 for one or more different parameters, including different technologies, features, subscriber preferences, hardware, software, technology, and/or methods. For example, each control panel 105 may be related to one or more discrete structures (e.g., a home, a business) and each of the one more discrete structures may be related to one or more discrete areas. In other examples, multiple control panels 105 may be related to the same one or more discrete structures (e.g., multiple control panels relating to a home and/or a business complex).

The devices 115 may be dispersed throughout the communications system 100 and each device 115 may be stationary and/or mobile. A device 115 may include a cellular phone, a personal digital assistant (PDA), a wireless modem, a wireless communication device, a handheld device, a tablet computer, a laptop computer, a cordless phone, a wireless local loop (WLL) station, a display device (e.g., TVs, computer monitors, etc.), a printer, a camera, and/or the like. A device 115 may also include or be referred to by those skilled in the art as a user device, a smartphone, a BLUETOOTH® device, a Wi-Fi device, a mobile station, a subscriber station, a mobile unit, a subscriber unit, a wireless unit, a remote unit, a mobile device, a wireless device, a wireless communications device, a remote device, an access terminal, a mobile terminal, a wireless terminal, a remote terminal, a handset, a user agent, a mobile client, a client, and/or some other suitable terminology.

The control panels 105 may wirelessly communicate with the sensors 150 via one or more antennas. The sensors 150 may be dispersed throughout the communications system 100 and each sensor 150 may be stationary and/or mobile. A sensor 150 may include and/or be one or more sensors that sense: proximity, motion, temperatures, humidity, sound level, smoke, structural features (e.g., glass breaking, window position, door position), time, light geo-location data of a user and/or a device, distance, biometrics, weight, speed, height, size, preferences, light, darkness, weather, time, system performance, and/or other inputs that relate to a security and/or an automation system. A device 115 and/or a sensor 150 may be able to communicate through one or more wired and/or wireless connections with various components such as control panels, base stations, and/or network equipment (e.g., servers, wireless communication points, etc.) and/or the like.

The sensors 150 may be stationary sensors 150 positioned to track biometric information while a subject person is immobile or may be a mobile sensor 150 that a subject may wear to monitor biometrics. The sensors 150 may be programmed to record a variety of information such as oxygen level, breathing rate, heart rate, respiratory distress, electrodermal activity, brain wave activity, respiratory rate, auditory data such as coughing, snoring, etc., brain activity, blood pressure, and the like. The sensors 150 may additionally and/or alternatively include GPS tracking. The sensors 150 and the sensors 150 abilities may be customized to each subject person to ensure proper recordings and tracking is occurring. In some embodiments, the sensors 150 may communicate with devices 115 such as visual recording devices 115 to record visual data of a subject person. The visual data collected by the device 115 may be linked to the biometric data collected by the sensor 150.

The communication links 125 shown in communications system 100 may include uplink (UL) transmissions from a device 115 to a control panel 105, and/or downlink (DL) transmissions, from a control panel 105 to a device 115. The downlink transmissions may also be called forward link transmissions while the uplink transmissions may also be called reverse link transmissions. Each communication link 125 may include one or more carriers, where each carrier may be a signal made up of multiple sub-carriers (e.g., waveform signals of different frequencies) modulated according to the various radio technologies. Each modulated signal may be sent on a different sub-carrier and may carry control information (e.g., reference signals, control channels, etc.), overhead information, user data, etc. The communication links 125 may transmit bidirectional communications and/or unidirectional communications. Communication links 125 may include one or more connections, including but not limited to, 345 MHz, Wi-Fi, BLUETOOTH®, BLUETOOTH® Low Energy, cellular, Z-WAVE®, 802.11, peer-to-peer, LAN, WLAN, Ethernet, fire wire, fiber optic, and/or other connection types related to security and/or automation systems.

In some embodiments, of communications system 100, control panels 105 and/or devices 115 may include one or more antennas for employing antenna diversity schemes to improve communication quality and reliability between control panels 105 and devices 115. Additionally or alternatively, control panels 105 and/or devices 115 may employ multiple-input, multiple-output (MIMO) techniques that may take advantage of multi-path, mesh-type environments to transmit multiple spatial layers carrying the same or different coded data.

While the devices 115 may communicate with each other through the control panel 105 using communication links 125, each device 115 may also communicate directly with one or more other devices via one or more direct communication links 134. Two or more devices 115 may communicate via a direct communication link 134 when both devices 115 are in the geographic coverage area 110 or when one or neither devices 115 is within the geographic coverage area 110. Examples of direct communication links 134 may include Wi-Fi Direct, BLUETOOTH®, wired, and/or, and other P2P group connections. The devices 115 in these examples may communicate according to the WLAN radio and baseband protocol including physical and MAC layers from IEEE 802.11, and its various versions including, but not limited to, 802.11b, 802.11g, 802.11a, 802.11n, 802.11ac, 802.11ad, 802.11ah, etc. In other implementations, other peer-to-peer connections and/or ad hoc networks may be implemented within communications system 100.

If an alarm threshold is satisfied, the communications system 100 may record the data to determine what triggered an event. For example, the sensors 150 and device 115 may use the communication links 125 to transfer data to one or all of a control panel 105, a device 115 such as a mobile device or computing device, a remote server 145, or the like. The data may be stored for future use, or may be immediately available to a supervising adult. In some embodiments, the data may additionally and/or alternatively be transferred to emergency support personnel and/or a communication system provider for further analysis and/or response requests.

Figure 2:
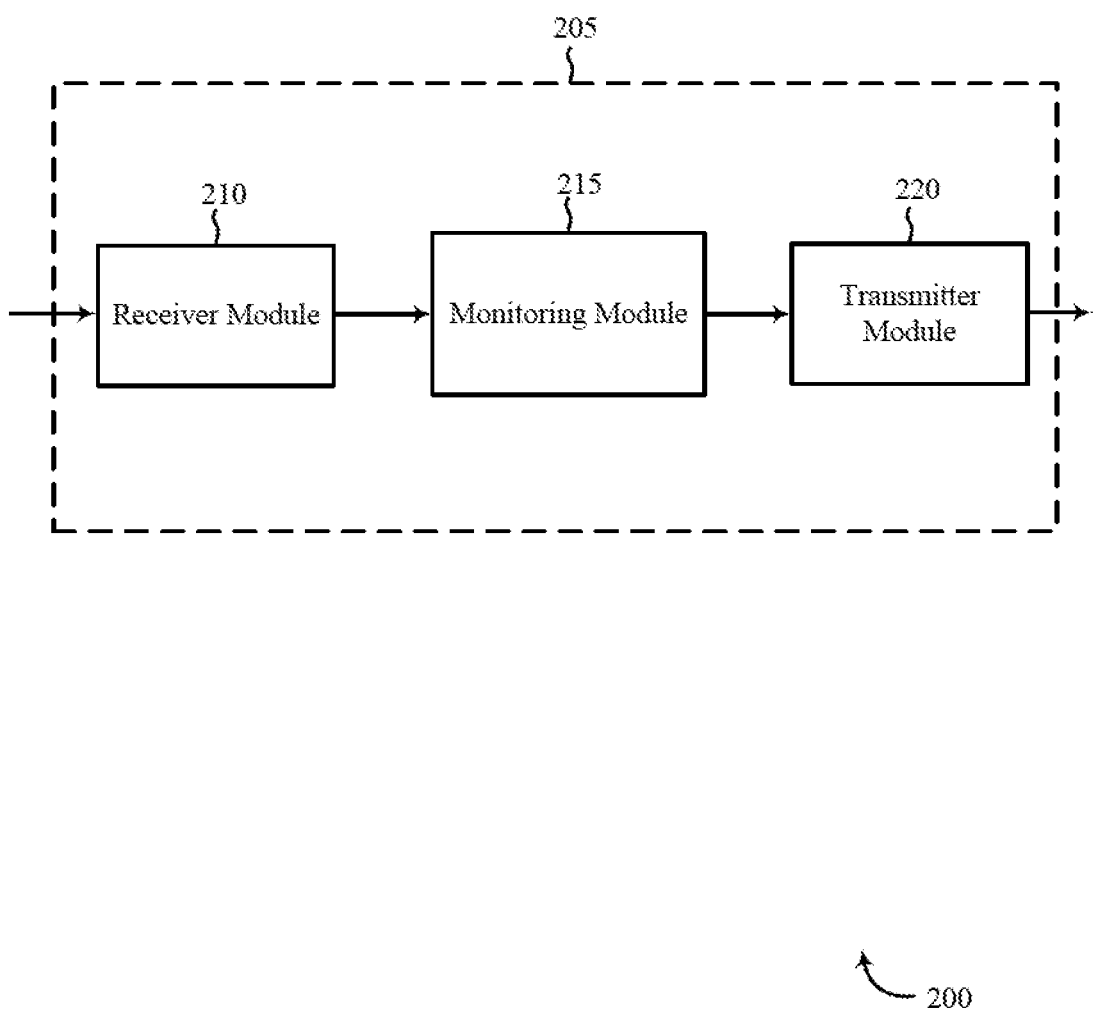
FIG. 2 shows a block diagram of a device relating to a security and/or an automation system, in accordance with various aspects of this disclosure.

FIG. 2 shows a block diagram 200 of a control panel 205 for use in electronic communication, in accordance with various aspects of this disclosure. The control panel 205 may be an example of one or more aspects of a control panel 105 described with reference to FIG. 1. The control panel 205 may include a receiver module 210, a monitoring module 215, and/or a transmitter module 220. The control panel 205 may also be or include a processor. Each of these modules may be in communication with each other—directly and/or indirectly.

The components of the control panel 205 may, individually or collectively, be implemented using one or more application-specific integrated circuits (ASICs) adapted to perform some or all of the applicable functions in hardware. Alternatively, the functions may be performed by one or more other processing units (or cores), on one or more integrated circuits. In other examples, other types of integrated circuits may be used (e.g., Structured/Platform ASICs, Field Programmable Gate Arrays (FPGAs), and other Semi-Custom ICs), which may be programmed in any manner known in the art. The functions of each module may also be implemented—in whole or in part—with instructions embodied in memory formatted to be executed by one or more general and/or application-specific processors.

The receiver module 210 may receive information such as packets, user data, and/or control information associated with various information channels (e.g., control channels, data channels, etc.). The receiver module 210 may be configured to receive visual recordings and/or biometric readings. Information may be passed on to the monitoring module 215, and to other components of the control panel 205.

The monitoring module 215 may monitor the well-being of a subject person. The subject person may comprise a variety of persons with various attributes. The subject person may be an infant or child that a parent or caregiver may wish to monitor. The subject person may be a person with a disability or disease that may affect their health. For example, the subject person may have epilepsy and be subject to seizure. The subject person may have narcolepsy and be subject to random sleep attacks. In another example, the subject person may be an adult with Alzheimer's or Lou Gehrig's disease. These diseases may affect a person's ability to live independently. Alternatively, the persons with these diseases may live independently and use monitoring as a means to safely live independently.

The monitoring module 215 may monitor various physical, emotional, and mental attributes of the subject person. The monitoring may reveal that a health-related event occurred or may be about to occur. For example, respiratory distress may be an example of an asthma attack. The blood-oxygen sensor may trigger a hypoxemia reading. Hypoxemia may be a sign of anemia, acute respiratory distress syndrome, heart defects, pulmonary fibrosis, sleep apnea, among others. The various sensors and readings may be funneled into an alarm threshold which may filter sensor readings to determine a viable alert.

The alert may transfer viable sensor information to various sources. The alert may generate at a control panel 205 and may transfer the information to a supervising adult. In some instances, the alert may transfer immediately to emergency personnel. The alert information may additionally be sent to a remote server (e.g. remote server 145). The alert may also transfer to monitoring personnel associated with the automation system which may take action as necessary.

The transmitter module 220 may transmit the one or more signals received from other components of the control panel 205. The transmitter module 220 may transmit various sensor information, visual recordings and/or alert information. In some examples, the transmitter module 220 may be collocated with the receiver module 210 in a transceiver module.

Figure 3:
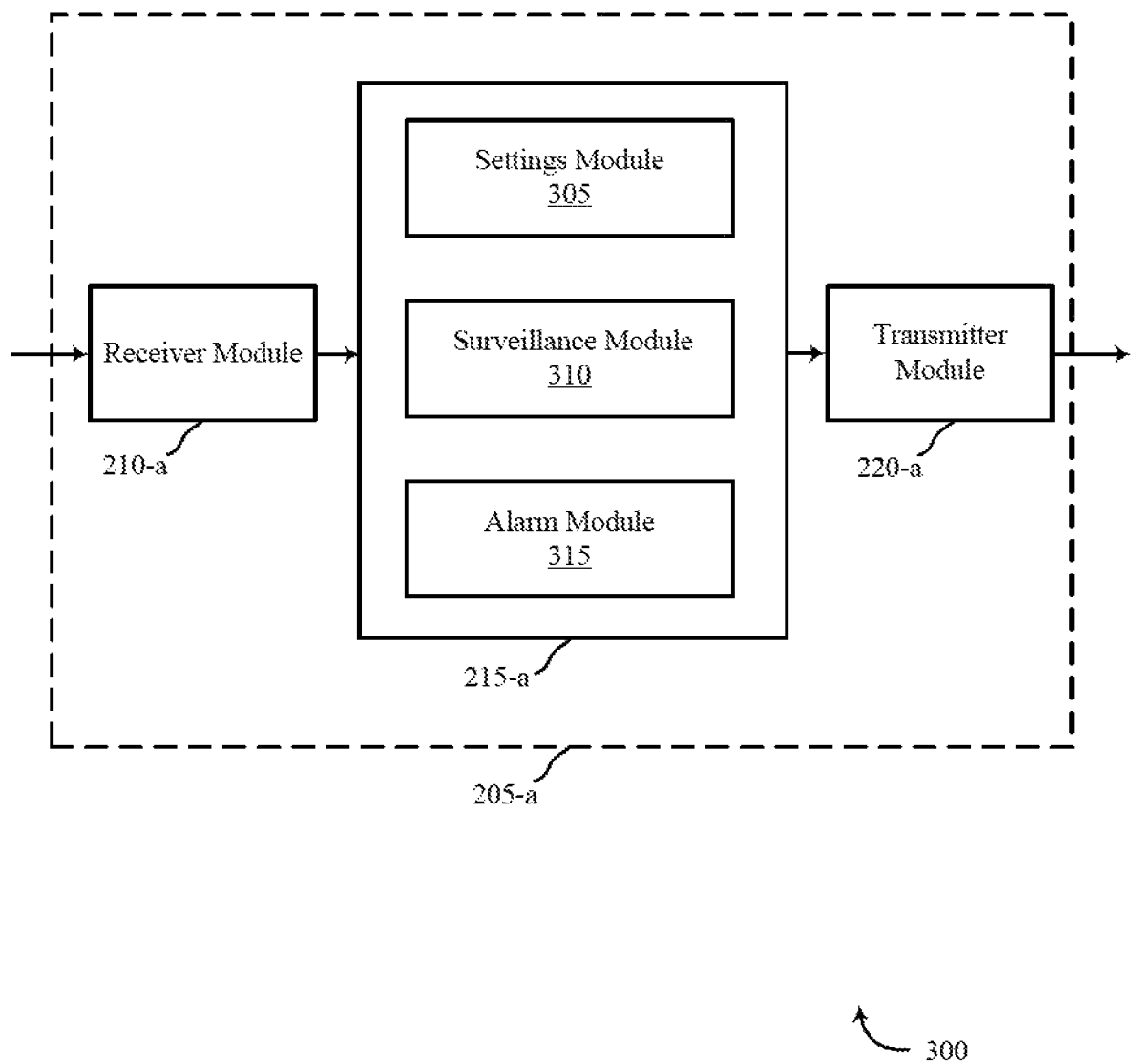
FIG. 3 shows a block diagram of a device relating to a security and/or an automation system, in accordance with various aspects of this disclosure.

FIG. 3 shows a block diagram 300 of a control panel 205-a for use in wireless communication, in accordance with various examples. The control panel 205-a may be an example of one or more aspects of a control panel 105 described with reference to FIG. 1. It may also be an example of a control panel 205 described with reference to FIG. 2. The control panel 205-a may include a receiver module 210-a, a monitoring module 215-a, and/or a transmitter module 220-a, which may be examples of the corresponding modules of control panel 205. The control panel 205-a may also include a processor. Each of these components may be in communication with each other. The monitoring module 215-a may include a settings module 305, a surveillance module 310, and an alarm module 315. The receiver module 210-a and the transmitter module 220-a may perform the functions of the receiver module 210 and the transmitter module 220, of FIG. 2, respectively.

The components of the control panel 205-a may, individually or collectively, be implemented using one or more application-specific integrated circuits (ASICs) adapted to perform some or all of the applicable functions in hardware. Alternatively, the functions may be performed by one or more other processing units (or cores), on one or more integrated circuits. In other examples, other types of integrated circuits may be used (e.g., Structured/Platform ASICs, Field Programmable Gate Arrays (FPGAs), and other Semi-Custom ICs), which may be programmed in any manner known in the art. The functions of each module may also be implemented—in whole or in part—with instructions embodied in memory formatted to be executed by one or more general and/or application-specific processors.

The settings module 305 may track the various settings to record for a subject person. The settings may include various biometric features. The settings may additionally and/or alternatively track movement and/or location. In some embodiments, the settings may include visual recordings.

The biometric feature settings may be specific to the individual. For example, infant monitoring may include respiratory rate, pulse, heart rate, blood pressure, temperature, and/or blood oxygen levels. These settings may be indicative of various abnormalities associated with infants such as sudden infant death syndrome. The settings may include the biometric features to be monitored and alarm thresholds. For example, the pulse and heart rate of an infant may be set to a different standard that the pulse and heart rate of an older child. An infant may have a heart rate of 80-140 bpm whereas a school age child may have a heart rate of 70-110 bpm. Similarly, a newborn may have a heart rate of 120-160 bpm.

Adult monitoring or specialized monitor may be very specific to a subject person and a known condition. If a person is diabetic, the sensors may monitor blood sugar levels. The settings may additionally include various indicators of a diabetic shock or hypoglycemia. Some examples of settings that may be tracked include shakiness, sweating, rapid heartbeat, fainting, seizure indicators, crying out in a sleep state, and the like. These settings may be monitored 24/7 to ensure a diabetic person is healthy and safe.

Alternatively, some conditions may only be monitored at specific times. For example, the settings module 305 may receive information to monitor a person with sleep apnea. This may reduce monitoring to a sleep state of the subject person since sleep apnea is occurs during sleep.

The settings module 305 may also include reactive settings. For example, the settings module 305 may set alarm thresholds and may additionally set actions to take when alarm thresholds are satisfied. In some instances, reaction settings may include transferring the collected biometric data and visual recordings of the event to a supervising person immediately after an event occurs. In other embodiments, the biometric data may be filtered prior to transferring information to a supervising person.

The surveillance module 310 may track the various biometric settings that are set. This may include recording sensor information and/or visual information. In some embodiments, the subject person may wear the sensors on their person to track the biometric parameters. The sensors may couple with recording devices to track a person's movement. For example, a residence may be equipped with various recording devices. When a person enters a room, the sensors may trigger a recording device which may visually record the movement of the subject person.

In some embodiments, the surveillance module 310 may track a subject person's stationary movement. For example, a sensor may include an accelerometer or similarly capable unit which may detect local movement. The local movement may be indicative of a seizure, sudden fall, or other unsettling movement. The surveillance module 310 may additionally track a person's location. The location tracking may be GPS-enabled. The location tracking may enable a supervising person or emergency personnel to respond to a situation at the correct setting. For example, if an adult with epilepsy is outside of the home, the sensors may still communicate with the automation system. If a seizure is detected, the control panel 205-a may request emergency personnel to respond. The surveillance module 310 may transfer the biometric information as well as the GPS location.

The alarm module 315 may filter the surveillance information to determine if an alarm threshold has been satisfied. The alarm module 315 may receive all the biometric information and may analyze the information to determine if a specific event is occurring, such as SIDS, hypoxemia, hypoglycemia, seizure, sleep apnea, or a like event. The alarm module 315 may additionally analyze visual recordings to determine if the biometric information matches physical action. For example, the alarm module 315 may receive information indicating an extreme jarring motion coupled with rapid breathing. The alarm module 315 may determine a seizure is occurring and, in some embodiments, may confirm the seizure with the visual recordings. In another embodiment, the alarm module 315 may receiving biometric data indicating a pause in breathing, a percentage of normal respiratory cycle, and an accelerated heart rate. These biometric factors may indicate the person is experiencing sleep apnea. In another embodiment, the alarm module 315 may receive biometric data indicating a coughing frequency (i.e., the auditory sensor may track the number of times a person coughs in relation to a predetermined time duration) and the intensity and/or force of the breathing (i.e., a breathing sensor may track the energy required to breath). The alarm module 315 may filter this information to conclude the person is suffering from sleep disordered breathing. In yet another embodiment, the alarm module 315 may receive information indicating a cessation of heart rate and breathing. The alarm module 315 may immediately determine emergency resuscitation is required and automatically contact emergency personnel to respond.

If an alarm threshold is satisfied, the alarm module 315 may transform the information and a visual recording of the event to a supervising person. The supervising person may be an adult monitoring the situation, the automation system itself, emergency personnel, and/or automation system controller personnel.

The supervising person may be onsite or may be remote. For example, a parent will likely be in the same residence as a their infant. The settings module 305 may track when a supervising person is at hand. The alarm module 315 may activate an audible alarm when an alarm threshold is satisfied. This may enable the supervising adult to take immediate action and attend to the subject person. The audible alarm may comprise a household alarm or may link to a device such as a control panel, computing device, or mobile device.

In alternative embodiments, the alarm may be an audio-visual alarm. For example, the alarm may create an audible reading and may also include a visual reading such as a light flashing. The visual alarm may additionally include activation of the visual surveillance recorded when the alarm threshold was satisfied. This type of visual alarm may automatically illuminate on a control panel, computing device, and/or mobile device.

However, an adult may transfer the alert information to a person not in their direct vicinity. For example, an elderly parent may transfer alert information to an adult child. The supervising person, when remote, may be local to offer real time assistance, or may be very distant. If the supervising person is remote, the supervising may be equipped to request emergency personnel assistance.

Once emergency personnel is contacted, the supervising adult may request biometric information to be transferred to the emergency personnel. Alternatively, the alarm module 315 may automatically transfer the biometric parameter readings to the emergency personnel. Visual recordings may additionally be transferred to emergency personnel.

Figure 4:
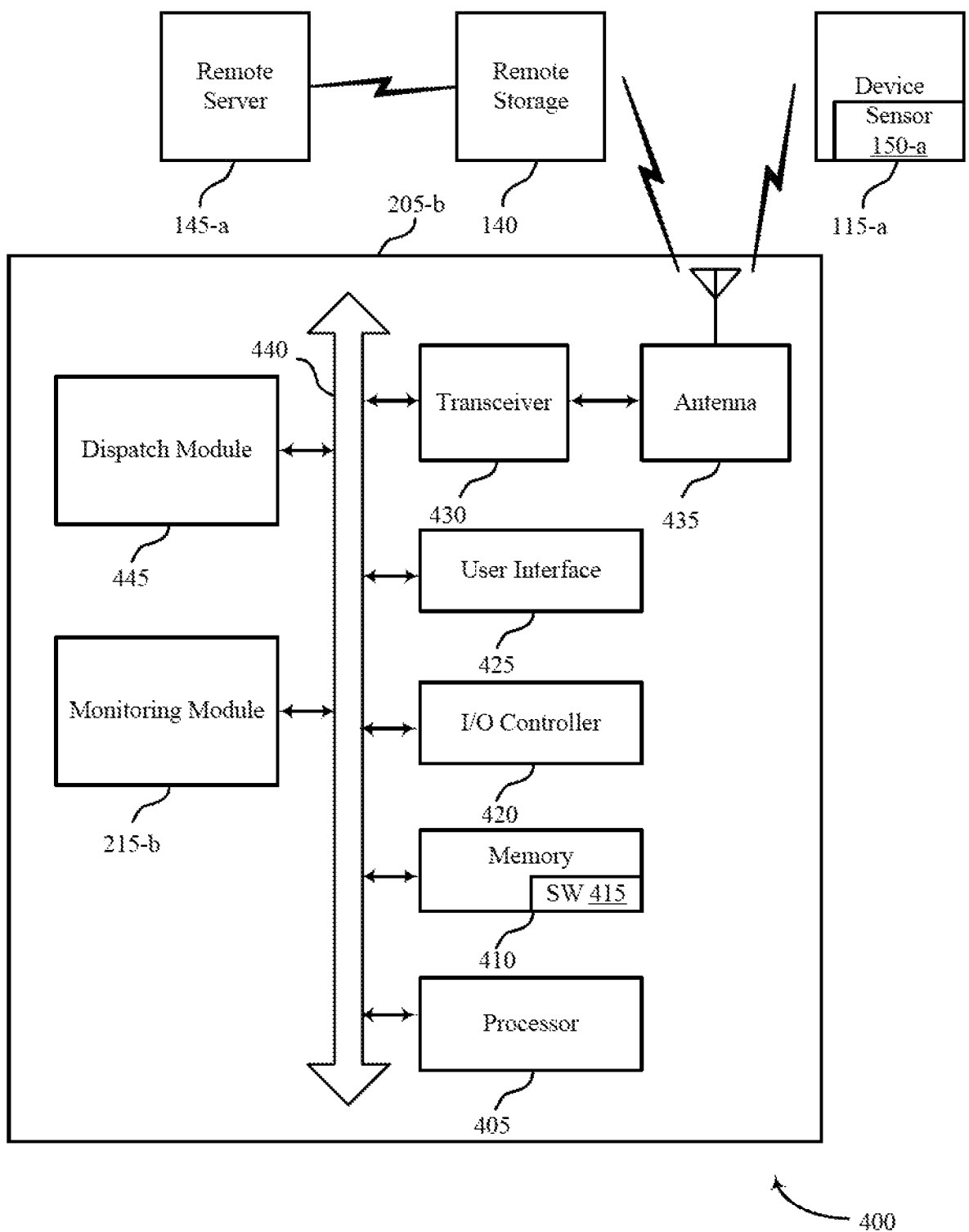
FIG. 4 shows a block diagram relating to a security and/or an automation system, in accordance with various aspects of this disclosure.

FIG. 4 shows a system 400 for use in biometric monitoring systems, in accordance with various examples. System 400 may include a control panel 205-*b*, which may be an example of the control panels 105 of FIG. 1. Control panel 205-*b* may also be an example of one or more aspects of control panels 205 and/or 205-*a* of FIGS. 2 and 3.

Control panel 205-*b* may include dispatch module 445. The control panel 205-*b* may also include a monitoring module 215-*b*, which may be an example of monitoring module 215 described with reference to FIGS. 2 and/or 3. In some embodiments, the terms a control panel and a control device are used synonymously.

Control panel 205-*b* may also include components for bi-directional voice and data communications including components for transmitting communications and components for receiving communications. For example, control panel 205-*b* may communicate bi-directionally with one or more of device 115-*a*, one or more sensors 150-*a*, remote storage 140, and/or remote server 145-*a*, which may be an example of the remote server of FIG. 1. This bi-directional communication may be direct (e.g., control panel 205-*b* communicating directly with remote storage 140) or indirect (e.g., control panel 205-*b* communicating indirectly with remote server 145-*a* through remote storage 140).

The dispatch module 445 may interface with emergency personnel based at least in part on alarm threshold parameters as described above with reference to FIG. 3. For example, the dispatch module 445 may connect to emergency personnel in an event situation and relay information pertaining to the event. The event may equate to an alarm status or satisfaction of an alarm threshold. In some instances, the monitoring module 215-*b* may be automatically equipped to connect and transfer information to emergency personnel via the dispatch module 445. In other embodiments, a supervising person may request emergency personnel and/or transfer information to the emergency personnel via the dispatch module 445.

Control panel 205-*b* may also include a processor module 405, and memory 410 (including software/firmware code (SW) 415), an input/output controller module 420, a user interface module 425, a transceiver module 430, and one or more antennas 435 each of which may communicate—directly or indirectly—with one another (e.g., via one or more buses 440). The transceiver module 430 may communicate bi-directionally—via the one or more antennas 435, wired links, and/or wireless links—with one or more networks or remote devices as described above. For example, the transceiver module 430 may communicate bi-directionally with one or more of device 115-*a*, remote storage 140, and/or remote server 145-*a*. The transceiver module 430 may include a modem to modulate the packets and provide the modulated packets to the one or more antennas 435 for transmission, and to demodulate packets received from the one or more antenna 435. While a control panel or a control device (e.g., 205-*b*) may include a single antenna 435, the control panel or the control device may also have multiple antennas 435 capable of concurrently transmitting or receiving multiple wired and/or wireless transmissions. In some embodiments, one element of control panel 205-*b* (e.g., one or more antennas 435, transceiver module 430, etc.) may provide a direct connection to a remote server 145-*a* via a direct network link to the Internet via a POP (point of presence). In some embodiments, one element of control panel 205-*b* (e.g., one or more antennas 435, transceiver module 430, etc.) may provide a connection using wireless techniques, including digital cellular telephone connection, Cellular Digital Packet Data (CDPD) connection, digital satellite data connection, and/or another connection.

The signals associated with system 400 may include wireless communication signals such as radio frequency, electromagnetics, local area network (LAN), wide area network (WAN), virtual private network (VPN), wireless network (using 802.11, for example), 345 MHz, Z-WAVE®, cellular network (using 3G and/or LTE, for example), and/or other signals. The one or more antennas 435 and/or transceiver module 430 may include or be related to, but are not limited to, WWAN (GSM, CDMA, and WCDMA), WLAN (including BLUETOOTH® and Wi-Fi), WMAN (WiMAX), antennas for mobile communications, antennas for Wireless Personal Area Network (WPAN) applications (including RFID and UWB). In some embodiments, each antenna 435 may receive signals or information specific and/or exclusive to itself. In other embodiments, each antenna 435 may receive signals or information not specific or exclusive to itself.

In some embodiments, one or more sensors 150-*a* (e.g., motion, proximity, smoke, light, glass break, door, window, carbon monoxide, and/or another sensor) may connect to some element of system 400 via a network using one or more wired and/or wireless connections.

In some embodiments, the user interface module 425 may include an audio device, such as an external speaker system, an external display device such as a display screen, and/or an input device (e.g., remote control device interfaced with the user interface module 425 directly and/or through I/O controller module 420).

One or more buses 440 may allow data communication between one or more elements of control panel 205-*b* (e.g., processor module 405, memory 410, I/O controller module 420, user interface module 425, etc.).

The memory 410 may include random access memory (RAM), read only memory (ROM), flash RAM, and/or other types. The memory 410 may store computer-readable, computer-executable software/firmware code 415 including instructions that, when executed, cause the processor module 405 to perform various functions described in this disclosure (e.g., monitor biometric information, record subject personnel, transfer information, activate an alarm status, etc.). Alternatively, the software/firmware code 415 may not be directly executable by the processor module 405 but may cause a computer (e.g., when compiled and executed) to perform functions described herein. Alternatively, the computer-readable, computer-executable software/firmware code 415 may not be directly executable by the processor module 405 but may be configured to cause a computer (e.g., when compiled and executed) to perform functions described herein. The processor module 405 may include an intelligent hardware device, e.g., a central processing unit (CPU), a microcontroller, an application-specific integrated circuit (ASIC), etc.

In some embodiments, the memory 410 can contain, among other things, the Basic Input-Output system (BIOS) which may control basic hardware and/or software operation such as the interaction with peripheral components or devices. For example, the dispatch module 445 and/or the monitoring module 215-*b* to implement the present systems and methods may be stored within the system memory 410. Applications resident with system 400 are generally stored on and accessed via a non-transitory computer readable medium, such as a hard disk drive or other storage medium. Additionally, applications can be in the form of electronic signals modulated in accordance with the application and data communication technology when accessed via a network interface (e.g., transceiver module 430, one or more antennas 435, etc.).

Many other devices and/or subsystems may be connected to one or may be included as one or more elements of system 400 (e.g., entertainment system, computing device, remote cameras, wireless key fob, wall mounted user interface device, cell radio module, battery, alarm siren, door lock, lighting system, thermostat, home appliance monitor, utility equipment monitor, and so on). In some embodiments, all of the elements shown in FIG. 4 need not be present to practice the present systems and methods. The devices and subsystems can be interconnected in different ways from that shown in FIG. 4. In some embodiments, an aspect of some operation of a system, such as that shown in FIG. 4, may be readily known in the art and are not discussed in detail in this application. Code to implement the present disclosure can be stored in a non-transitory computer-readable medium such as one or more of system memory 410 or other memory. The operating system provided on I/O controller module 420 may be iOS®, ANDROID®, MS-DOS®, MS-WINDOWS®, OS/2®, UNIX®, LINUX®, or another known operating system.

The transceiver module 430 may include a modem configured to modulate the packets and provide the modulated packets to the antennas 435 for transmission and/or to demodulate packets received from the antennas 435. While the control panel or control device (e.g., 205-*b*) may include a single antenna 435, the control panel or control device (e.g., 205-*b*) may have multiple antennas 435 capable of concurrently transmitting and/or receiving multiple wireless transmissions.

Figure 5:
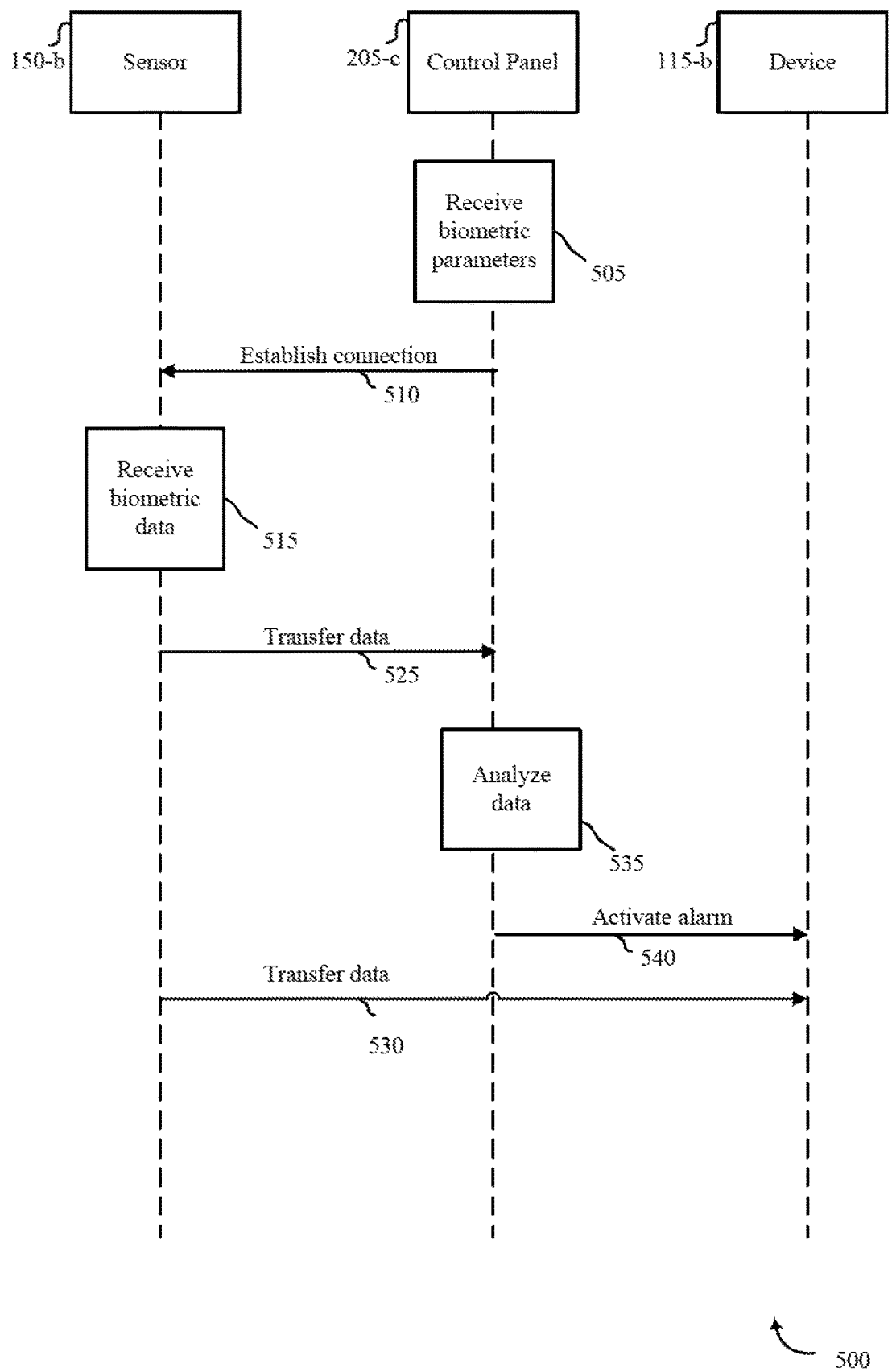
FIG. 5 shows a swim diagram relating to a security and/or an automation system, in accordance with various aspects of this disclosure

FIG. 5 is a swim diagram 500 illustrating communication relating to a sensor 150-*b*, a control panel 205-*c*, and a device 115-*b* relating to an automation system. The sensor 150-*b* may be one example of sensor 150 described with reference to FIGS. 1 and/or 4, among others. The control panel 205-*c* may be one example of control panel 105 and/or control panel 205 described with reference to FIGS. 1-4. The device 115-*b* may be one example of device 115 described with reference to FIGS. 1 and/or 4.

At block 505, the control panel 205-*c* may receive biometric parameters. The parameters may include various biometric readings discussed herein. For example the parameters may include blood pressure, blood oxygen level, breathing rate, heart rate, respiratory distress, electro dermal activity, brain wave activity, tremors, and the like. The parameters may include monitoring parameters such as time, location, duration, and the like. For example, babies may only be monitored at night or while they are in their crib. Adults with various conditions may be continuously monitored. Seniors may be continuously monitored. If a person had a concussion, the person may be monitored for a predetermined time duration after the concussion to determine if any lasting effects are present. The parameters may additionally include visual recording settings. The visual recording may be present at all times the subject person is proximate the home, or alternatively, may be limited to specific time periods such as night hours, day hours, or the like.

The control panel 205-*c* may then establish a connection 510 with various sensors 150-*b* to monitor the biometric parameters. The control panel 205-*c* may additionally connect to one or more recording devices to receive visual data on the subject person. The sensors 150-*b*, once activated may receive biometric data 515 from the subject person. The sensors 150-*b* may coordinate with a video device to time sync the biometric data with visual data. The data may be transferred 525 to the control panel 205-*c*. The control panel 205-*c* may filter the results to determine if an event is occurring. The event may be linked to alarm thresholds which may indicate less than desirable health in the individual. The thresholds may be markers for known attributes associated with the subject person. For example the thresholds may be keyed towards SIDS, hypoxemia, hypoglycemia, or the like. The control panel 205-*c* may additionally run generic analysis against known medical conditions to determine if an unexpected event is occurring such as a stroke or heart attack.

The control panel 205-*b* may then activate an alarm 540 and alert a supervising person via a device 115-*b*. The device 115-*b* may be a mobile device associated with the supervising person. IN some embodiments the alarm activation may occur at the control panel 205-*c* and result in an audible alarm. Visual recordings of the event may display automatically on the control panel 205-*c* and/or device 115-*b*. The alarm may continue to sound until input is received from a user to deactivate the alarm. The sensors 150-*b* proximate the subject person may be able to deactivate the alarm or a separate sensor may deactivate the alarm. In some embodiments, if the biometric parameters return to normal, the alarm may cease. In some embodiments, the alarm may be scaled. For example, at signs of distress, a first alarm may sound. As the distress level increases and the biometric parameters indicate an increasingly worrisome issue, the alarm may increase in volume, frequency, or the like.

In some embodiments, the sensors 150 may transfer data 530 directly to the supervising personnel via the device 115-*b*. The supervising person may be able to use a mobile device to view live streaming biometric data and visual information. This may enable a supervising person to feel at ease. In some instances, the biometric information may be helpful even if the supervising person is next to the subject person. A supervising person may not have the knowledge to understand when a person is having a stroke or a seizure or a heart attack. The biometric parameters and alarm threshold may enable the supervising person to react quickly to specific situations using the specialized information.

Figure 6:
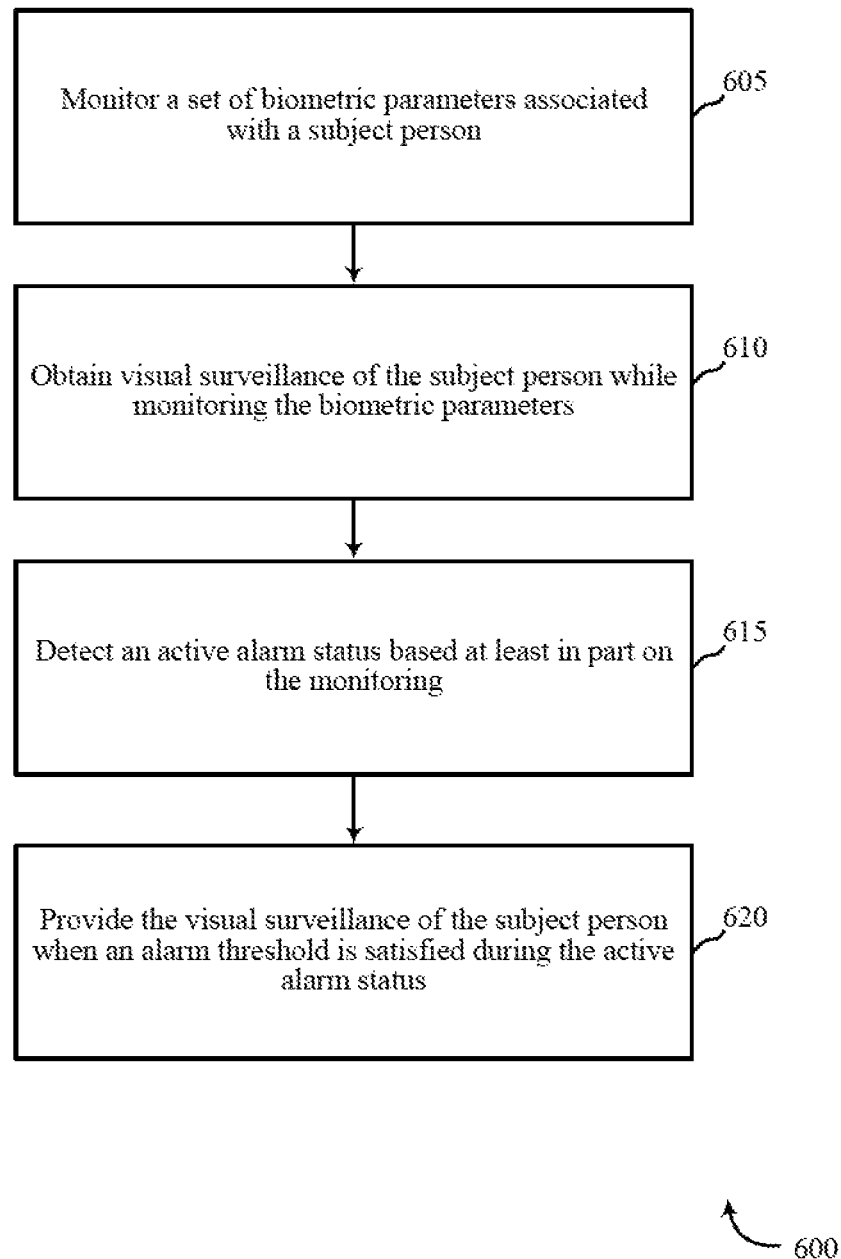
FIG. 6 is a flow chart illustrating an example of a method relating to a security and/or an automation system, in accordance with various aspects of this disclosure.

FIG. 6 is a flow chart illustrating an example of a method 600 for biometric monitoring of a subject person, in accordance with various aspects of the present disclosure. For clarity, the method 700 is described below with reference to aspects of one or more of the sensors 150 and/or device 115 described with reference to FIG. 1, 4, or 5, and/or aspects of one or more of the control panel 105 or control panel 205 described with reference to FIGS. 1-5. In some examples, a control panel may execute one or more sets of codes to control the functional elements of the sensor and/or devices to perform the functions described below. Additionally or alternatively, the control panel may perform one or more of the functions described below using special-purpose hardware.

At block 605, the method 600 may include monitoring a set of biometric parameters associated with a subject person. The biometric parameters may include blood pressure, blood oxygen level, breathing rate, heart rate, respiratory distress, electro dermal activity, brain wave activity, tremors, blood pressure, brain activity, auditory data, and the like. The parameters may include monitoring parameters such as time, location, duration, volume, and the like. For example, adults with known conditions may be continuously monitored despite their location. If an adult is away from their home setting, the sensors may be equipped to transfer the biometric data to the control panel. In another embodiment, the sensors may transfer the biometric data to their mobile device. In those embodiments, the mobile device may be enabled for analyzing the data.

The operation(s) at block 605 may be performed using the settings module 305 and/or the surveillance module 310 described with reference to FIG. 3.

At block 610, the method 600 may include obtaining visual surveillance of the subject person while monitoring the biometric parameters. The visual surveillance may be predetermined such as video surveillance of an infant in their crib. The visual surveillance may also include monitoring an individual with dementia in the kitchen or a person with sleep apnea while they sleep. In other embodiments, the visual surveillance may be triggered by location of the person. The subject person may have a sensor which may trigger local cameras to activate and track the person, recording visual data. As a person moves through the house, the various video feeds may be combined into a seamless video for the supervising person to view.

The operation(s) at block 610 may be performed using the surveillance module 310 described with reference to FIG. 3.

At block 615, the method 600 may include detecting an active alarm status based at least in part on the monitoring. The active alarm status may include analyzing the biometric data to determine if a health event is occurring. Analyzing the biometric data may include assessing the biometric parameters to determine if different combinations of the information are indicative of health concerns. The active alarm may include an audible alarm or an audio-visual alarm.

At block 620, the method 600 may include providing the visual surveillance of the subject person when an alarm threshold is satisfied during the active alarm status. For example, the visual surveillance may be recorded either locally on the control panel or remote on a remote server. This may enable the visual surveillance to be viewed at a later data if it is stored on a database. Alternatively, if there is an active alarm status, the supervising person may receive a video recording of the event immediately after the event occurs. This may enable the supervising person to determine next actions. For example, the alarm event may be as simple as a monitor falling off a baby. A sudden fall alarm may equate to a person jumping, and the like. The video recording may enable the supervising person to determine a severity of the event and request proper support. In some embodiments, proper support may include request emergency personnel.

The operation(s) at block 610 may be performed using the alarm module 315 described with reference to FIG. 3.

Thus, the method 600 may provide for obtaining visual surveillance of the subject person while monitoring the biometric parameters relating to automation/security systems. It should be noted that the method 700 is just one implementation and that the operations of the method 600 may be rearranged or otherwise modified such that other implementations are possible.

Figure 7:
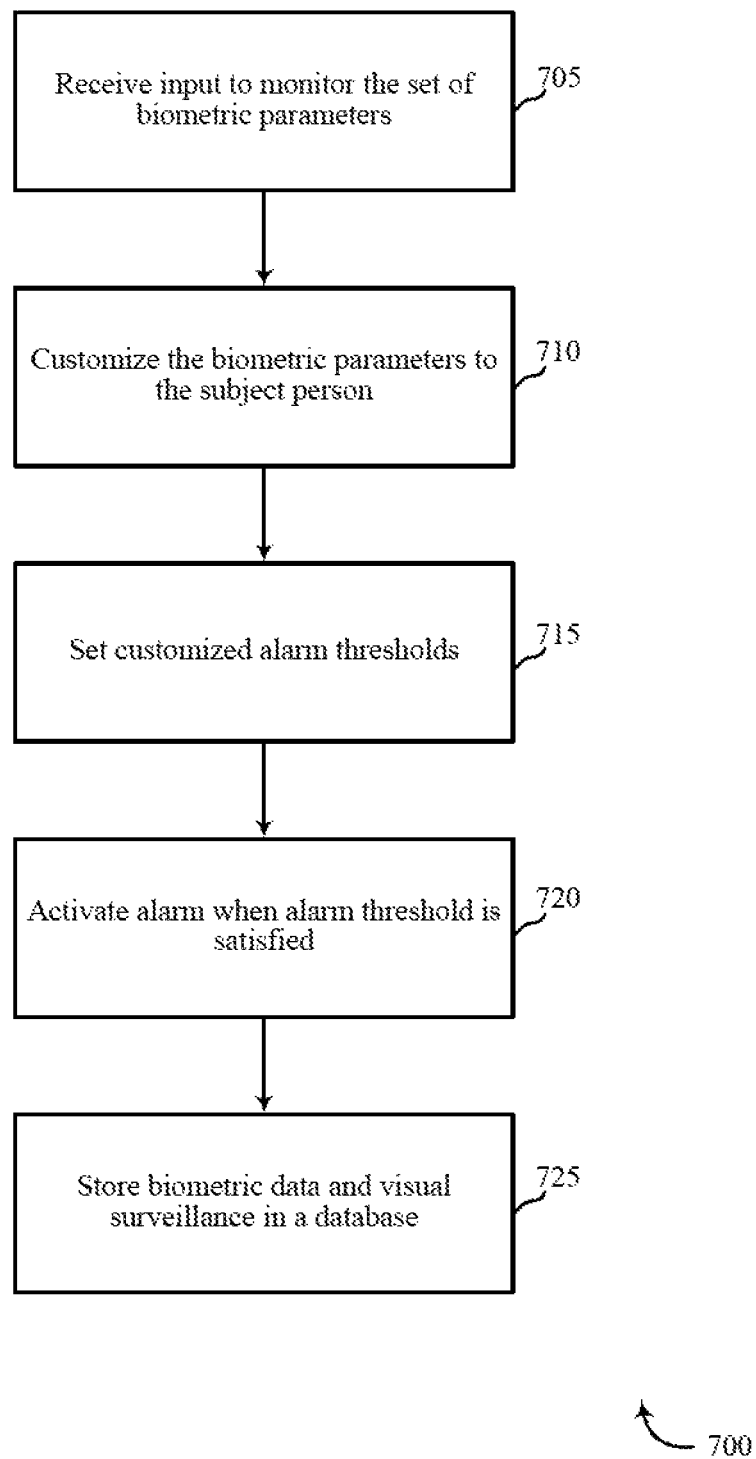
FIG. 7 is a flow chart illustrating an example of a method relating to a security and/or an automation system, in accordance with various aspects of this disclosure.

FIG. 7 is a flow chart illustrating an example of a method 700 for biometric monitoring of a subject person, in accordance with various aspects of the present disclosure. For clarity, the method 700 is described below with reference to aspects of one or more of the sensors 150 and/or device 115 described with reference to FIG. 1, 4, or 5, and/or aspects of one or more of the control panel 105 or control panel 205 described with reference to FIGS. 1-5. In some examples, a control panel may execute one or more sets of codes to control the functional elements of the sensor and/or devices to perform the functions described below. Additionally or alternatively, the control panel may perform one or more of the functions described below using special-purpose hardware.

At block 705, the method 700 may include receiving input to monitor the set of biometric parameters. Monitoring the biometric parameters may include activating wearable technology equipped with special sensors to detect various biometric parameters. The wearable technology may additionally connect to local cameras to activate visual surveillance when the subject person is in the same vicinity.

At block 710, the method 700 may include customizing the biometric parameters to the subject person. For example, a child may have a certain set of parameters associated with their health. Alternatively, an autistic person may have other biometric parameters that indicate stressful situations. A person with vertigo may have another set of parameters. Each person will have a set of biometric parameters keyed to their health. The parameters themselves may need to be customized. For example, the heart rate of an infant will not coincide with the heart rate of an elderly person. Therefore, once a biometric parameter is set, an acceptable range must also be determined.

At block 715, the method 700 may include setting customized alarm thresholds. Again, the alarm thresholds may be unique to a person. For example, a diabetic person may have a narrower range of acceptable glucose in their system than a "healthy" person. Similarly, an adult may have varying blood pressure levels based on their overall health. For the alarm to be effective, each acceptable biometric range but be keyed to the subject person. In some embodiments, there may be a learning curve where thresholds are conservative to ensure all health concerns are captured and may be altered over time to perfect the alarm threshold and/or react to changing health conditions.

The operation(s) at block 705-715 may be performed using the settings module 305 and/or the surveillance module 310 described with reference to FIG. 3.

At block 720, the method 700 may include activating an alarm when an alarm threshold is satisfied. The alarm threshold may be a combination of thresholds to activate an alarm. Alternatively, a single biometric reading may activate the alarm. The alarm may be an audible alarm. For example, a loud noise may emit from an automation system in every room in a house. Alternatively, if home monitoring, a small alarm module may be carried by the supervising person. The supervising person may also use their mobile device to receive an audible alarm. In other embodiments the alarm may have a visual component. The visual component may be a flashing light. Alternatively, the visual component may comprise playing a video recording of the event. The video recording may play automatically on a control, small alarm module, mobile device, television, tablet, computing device, or the like.

At block 725, the method 700 may include storing biometric data and visual surveillance in a database. The database may be local such as a part of the control panel. The database may additionally or alternatively comprise remote storage (e.g. remote server). The data may be stored for a predetermined time before being erased. The data may enable a person to review the health history of the subject person for a predetermined period of time. In some embodiments, this may be indicative of health trends such as improving health or worsening health. The method 700 may review the data to determine if these trends exist.

The operation(s) at block 720-725 may be performed using the alarm module 315 described with reference to FIG. 3.

Thus, the method 700 may provide for obtaining visual surveillance of the subject person while monitoring the biometric parameters relating to automation/security systems. It should be noted that the method 700 is just one implementation and that the operations of the method 700 may be rearranged or otherwise modified such that other implementations are possible.

In some examples, aspects from two or more of the methods 600, 700 may be combined and/or separated. It should be noted that the methods 600, 700, are just example implementations, and that the operations of the methods 700-[1000] may be rearranged or otherwise modified such that other implementations are possible.

The detailed description set forth above in connection with the appended drawings describes examples and does not represent the only instances that may be implemented or that are within the scope of the claims. The terms "example" and "exemplary," when used in this description, mean "serving as an example, instance, or illustration," and not "preferred" or "advantageous over other examples." The detailed description includes specific details for the purpose of providing an understanding of the described techniques. These techniques, however, may be practiced without these specific details. In some instances, known structures and apparatuses are shown in block diagram form in order to avoid obscuring the concepts of the described examples.

Information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and components described in connection with this disclosure may be implemented or performed with a general-purpose processor, a digital signal processor (DSP), an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, and/or state machine. A processor may also be implemented as a combination of computing devices, e.g., a combination of a DSP and a microprocessor, multiple microprocessors, one or more microprocessors in conjunction with a DSP core, and/or any other such configuration.

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope and spirit of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations.

As used herein, including in the claims, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination. Also, as used herein, including in the claims, "or" as used in a list of items (for example, a list of items prefaced by a phrase such as "at least one of" or "one or more of") indicates a disjunctive list such that, for example, a list of "at least one of A, B, or C" means A or B or C or AB or AC or BC or ABC (i.e., A and B and C).

In addition, any disclosure of components contained within other components or separate from other components should be considered exemplary because multiple other architectures may potentially be implemented to achieve the same functionality, including incorporating all, most, and/or some elements as part of one or more unitary structures and/or separate structures.

Computer-readable media includes both computer storage media and communication media including any medium that facilitates transfer of a computer program from one place to another. A storage medium may be any available medium that can be accessed by a general purpose or special purpose computer. By way of example, and not limitation, computer-readable media can comprise RAM, ROM, EEPROM, flash memory, CD-ROM, DVD, or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include compact disc (CD), laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The previous description of the disclosure is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not to be limited to the examples and designs described herein but is to be accorded the broadest scope consistent with the principles and novel features disclosed.

This disclosure may specifically apply to security system applications. This disclosure may specifically apply to automation system applications. In some embodiments, the concepts, the technical descriptions, the features, the methods, the ideas, and/or the descriptions may specifically apply to security and/or automation system applications. Distinct advantages of such systems for these specific applications are apparent from this disclosure.

The process parameters, actions, and steps described and/or illustrated in this disclosure are given by way of example only and can be varied as desired. For example, while the steps illustrated and/or described may be shown or discussed in a particular order, these steps do not necessarily need to be performed in the order illustrated or discussed. The various exemplary methods described and/or illustrated here may also omit one or more of the steps described or illustrated here or include additional steps in addition to those disclosed.

Furthermore, while various embodiments have been described and/or illustrated here in the context of fully functional computing systems, one or more of these exemplary embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. In some embodiments, these software modules may permit and/or instruct a computing system to perform one or more of the exemplary embodiments disclosed here.

This description, for purposes of explanation, has been described with reference to specific embodiments. The illustrative discussions above, however, are not intended to be exhaustive or limit the present systems and methods to the precise forms discussed. Many modifications and variations are possible in view of the above teachings. The embodiments were chosen and described in order to explain the principles of the present systems and methods and their practical applications, to enable others skilled in the art to utilize the present systems, apparatus, and methods and various embodiments with various modifications as may be suited to the particular use contemplated.

What is claimed is:

1. A method for a security and/or automation system, comprising:
   receiving, at a stationary control panel of the security and/or automation system associated with a structure, a set of alarm thresholds and a monitoring parameter, wherein the set of alarm thresholds are associated with a set of biometric parameters associated with a subject person;
   establishing a wireless connection between the stationary control panel and one or more sensors associated with the subject person based at least in part on the monitoring parameter;
   monitoring the set of biometric parameters and a location of the subject person within the structure based at least in part on establishing the wireless connection with the one or more sensors;
   activating a recording device to visually record the subject person in response to presence of the subject person in a room within the structure;
   activating an alarm based at least in part on detecting within the set of biometric parameters an indication of an abnormal medical condition of the subject person and confirming via analysis of the visual recording that physical actions of the subject person indicate an abnormal medical condition that matches the indication detected within the set of biometric parameters; and
   transmitting an alert to a supervising person based at least in part on activating the alarm.

2. The method of claim 1, further comprising:
   receiving a first biometric parameter within the set of biometric parameters from a first sensor and a second biometric parameter within the set of biometric parameters from a second sensor.

3. The method of claim 2, wherein monitoring the set of biometric parameters further comprises:
   assessing a combination of the first biometric parameter and the second biometric parameter; and
   determining whether the combination of the first biometric parameter and the second biometric parameter satisfies the set of alarm thresholds, wherein activating the alarm is based at least in part on the combination of the first biometric parameter and the second biometric parameter satisfying the set of alarm thresholds.

4. The method of claim 2, wherein the alarm comprises an audio alarm, and wherein activating the alarm comprises increasing a volume and a frequency of the audio alarm.

5. The method of claim 1, wherein the abnormal medical condition comprises at least one selected from the group of acute respiratory distress syndrome, stroke, heart attack, sudden infant syndrome, hypoxemia, hypoglycemia, seizure, sleep apnea, cessation of heart rate, rapid breathing, and cessation of breathing.

6. The method of claim 1, further comprising:
identifying the set of biometric parameters to be monitored for the subject person; and
customizing the set of biometric parameters based at least in part on historical data associated with the subject person.

7. The method of claim 1, wherein transmitting the alert to the supervising person comprises:
transferring, to the supervising person, biometric data and the visual recording of the subject person.

8. The method of claim 1, further comprising:
determining that at least one biometric parameter of the set of biometric parameters fails to satisfy the set of alarm thresholds; and
automatically deactivating the alarm based at least in part on determining that the at least one biometric parameter fails to satisfy the set of alarm thresholds.

9. The method of claim 1, wherein the monitoring parameter comprises at least one of a time to monitor the subject person, a location to monitor the subject person, and a duration to monitor the subject person.

10. An apparatus for a security and/or automation system, comprising:
a processor,
memory coupled with the processor; and
instructions stored in the memory and executable by the processor to cause the apparatus to:
receive, at a stationary control panel of the security and/or automation system associated with a structure, a set of alarm thresholds and a monitoring parameter, wherein the set of alarm thresholds are associated with a set of biometric parameters associated with a subject person;
establish a wireless connection between the stationary control panel and one or more sensors associated with the subject person based at least in part on the monitoring parameter;
monitor the set of biometric parameters and a location of the subject person within the structure based at least in part on establishing the wireless connection with the one or more sensors;
activate a recording device to visually record the subject person in response to presence of the subject person in a room within the structure;
activate an alarm based at least in part on detecting within the set of biometric parameters an indication of an abnormal medical condition of the subject person and confirming via analysis of the visual recording that physical actions of the subject person indicate an abnormal medical condition that matches the indication detected within the set of biometric parameters; and
transmit an alert to a supervising person based at least in part on activating the alarm.

11. The apparatus of claim 10, wherein the instructions are further executable by the processor to cause the apparatus to:
receive a first biometric parameter within the set of biometric parameters from a first sensor and a second biometric parameter within the set of biometric parameters from a second sensor.

12. The apparatus of claim 11, wherein the instructions to monitor the set of biometric parameters further are executable by the processor to cause the apparatus to:
assess a combination of the first biometric parameter and the second biometric parameter; and
determine whether the combination of the first biometric parameter and the second biometric parameter satisfies the set of alarm thresholds, wherein activating the alarm is based at least in part on the combination of the first biometric parameter and the second biometric parameter satisfying the set of alarm thresholds.

13. The apparatus of claim 11, wherein the alarm comprises an audio alarm, and wherein activating the alarm comprises increasing a volume and a frequency of the audio alarm.

14. The apparatus of claim 10, wherein the abnormal medical condition comprises at least one selected from the group of acute respiratory distress syndrome, stroke, heart attack, sudden infant syndrome, hypoxemia, hypoglycemia, seizure, sleep apnea, cessation of heart rate, rapid breathing, and cessation of breathing.

15. The apparatus of claim 10, wherein the instructions are further executable by the processor to cause the apparatus to:
identify the set of biometric parameters to be monitored for the subject person; and
customize the set of biometric parameters based at least in part on historical data associated with the subject person.

16. The apparatus of claim 10, wherein the instructions to transmit the alert to the supervising person are executable by the processor to cause the apparatus to:
transfer, to the supervising person, biometric data and the visual recording of the subject person.

17. The apparatus of claim 10, wherein the instructions are further executable by the processor to cause the apparatus to:
determine that at least one biometric parameter of the set of biometric parameters fails to satisfy the set of alarm thresholds; and
automatically deactivate the alarm based at least in part on determining that the at least one biometric parameter fails to satisfy the set of alarm thresholds.

18. The apparatus of claim 10, wherein the monitoring parameter comprises at least one of a time to monitor the subject person, a location to monitor the subject person, and a duration to monitor the subject person.

19. A non-transitory computer-readable medium storing code for a security and/or automation system, the code comprising instructions executable by a processor to:
receive, at a stationary control panel of the security and/or automation system associated with a structure, a set of alarm thresholds and a monitoring parameter, wherein the set of alarm thresholds are associated with a set of biometric parameters associated with a subject person;
establish a wireless connection between the stationary control panel and one or more sensors associated with the subject person based at least in part on the monitoring parameter;
monitor the set of biometric parameters and a location of the subject person relative to the structure based at least in part on establishing the wireless connection with the one or more sensors;
activate a recording device to visually record the subject person in response to presence of the subject person in a room within the structure;
activate an alarm based at least in part on detecting within the set of biometric parameters an indication of an abnormal medical condition of the subject person and confirming via analysis of the visual recording that physical actions of the subject person indicate an abnormal medical condition that matches the indication detected within the set of biometric parameters; and transmit an alert to a supervising person based at least in part on activating the alarm.

20. The non-transitory computer-readable medium of claim 19, wherein the instructions are further executable to:

receive a first biometric parameter within the set of biometric parameters from a first sensor and a second biometric parameter within the set of biometric parameters from a second sensor;

assess a combination of the first biometric parameter and the second biometric parameter; and determine whether the combination of the first biometric parameter and the second biometric parameter satisfies the set of alarm thresholds, wherein activating the alarm is based at least in part on the combination of the first biometric parameter and the second biometric parameter satisfying the set of alarm thresholds.

* * * * *